United States Patent [19]
Tamburini et al.

[11] Patent Number: 5,981,208
[45] Date of Patent: Nov. 9, 1999

[54] DIAGNOSTIC ASSAY FOR ALZHEIMER'S DISEASE BASED ON THE PROTEOLYSIS OF THE AMYLOID PRECURSOR PROTEIN

[75] Inventors: Paul P. Tamburini, Kensington; Robert N. Dreyer, Wallingford; Kathryn M. Bausch, West Haven, all of Conn.

[73] Assignee: Bayer Corporation, West Haven, Conn.

[21] Appl. No.: 08/319,339

[22] Filed: Oct. 6, 1994

Related U.S. Application Data

[63] Continuation of application No. 08/156,516, Nov. 23, 1993, abandoned, which is a continuation of application No. 07/865,167, Apr. 9, 1992, abandoned.

[51] Int. Cl.⁶ .................................................. G01N 33/53
[52] U.S. Cl. .............................. 435/23; 435/7.1; 436/518; 436/811
[58] Field of Search ........................... 435/7.1, 7.9, 7.92, 435/7.93, 7.94, 7.95, 23, 24, 975, 4; 436/501, 518, 528, 531, 811; 530/350

[56] References Cited

U.S. PATENT DOCUMENTS

| | | |
|---|---|---|
| 4,874,694 | 10/1989 | Gandy et al. . |
| 5,039,511 | 8/1991 | Quay et al. . |
| 5,200,324 | 4/1993 | Navaratnam et al. . |
| 5,200,339 | 4/1993 | Abraham . |

FOREIGN PATENT DOCUMENTS

| | | |
|---|---|---|
| 0 459 454 | 7/1996 | European Pat. Off. . |
| 90/14840 | 12/1990 | WIPO . |
| 92/03542 | 3/1992 | WIPO . |
| 9603153 | 2/1996 | WIPO . |

OTHER PUBLICATIONS

Kitaguchi et al Determination & Amyloid β Protein Precensors Harboring, Active Form Proteinase Inhibitor Domains in Cerebrospinal Fluid of Alzheimers Disease Patents by Tryspin Antibody Sanduech Elisa vol. 166, No. 3 pp. 1453–1459 Feb. 14, 1990.

Schilling, James, "Recombinant Alzheimers Amyloid Protein" WO 90/14840 Published Dec. 13, 1990.

Morris et al The Consortuim to Establish a Registry for Alzheimer's Disease (CERAD) Sep. 1989 Neurology 39:1159–1165.

Matsubara et al Serum Concentration of α, Antichymotrypsin in Patents With Senile Dementa of the Alzheimer's Type In: Iqbulk, et al eds. Alzheimers Disease and Related Disorders New York: Alan R. Liss 1989 :707–714.

Gollin et al., "α1 Antitrypsin and α1 Antichymotryspin are in the Lesins of Alzheimer's Disease" Neuro Report 3:201–203 Feb. 1992.

Abraham et al; Biochem Biophys Res Comm; 174 (2), 1991.
Bush et al; Jo Biol Chem, 265 (26) pp. 15977–15983, 1990.
Van Norstrand et al; Jo Biol. Chem, 265 (17) pp. 9591–9594, 1990.

Kang, The Precursor of Alzheimer's Disease Amyloid A4 Protein Resembles a Cell–Surface Receptor, Nature, vol.325:pp. 733–736, Feb. 19, 1987.

Wolozin et al., A Neuronal Antigen in the Brains of Alzheimer Patients, Science, vol.323:pp. 648–650 Feb. 18, 1986.

*Primary Examiner*—Paula K. Hutzell
*Assistant Examiner*—Patricia A. Duffy
*Attorney, Agent, or Firm*—Sprung Kramer Schaefer & Briscoe

[57] ABSTRACT

A method useful in the diagnosis of Alzheimer's Disease in a patient in which an amyloid protein precursor (APP) substrate is combined with a sample of cerebrospinal fluid or blood obtained from the patient to be tested, and poteolytic cleavage of the APP substrate is detected. The absence of detectable proteolytic cleavage, or the detection of a substantially lesser degree of proteolytic cleavage, in the presence of the patient's sample compared to that detected when an APP substrate is combined with test samples from control individuals, indicates affliction with Alzheimer's Disease. Convenient test reagents and kits for aiding the diagnosis of Alzheimer's Disease are provided, such as comprising an APP substrate and immunoreagents for detecting a fragment formed by proteolytic cleavage as well as chromogenic APP substrates.

5 Claims, 1 Drawing Sheet

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH:   39 nucleotides
        (B) TYPE:  nucleic acids
        (C) STRANDEDNESS: single strand
        (D) TOPOLOGY: linear (ii) MOLECULE TYPE:
            cDNA to mRNA (iii) PUBLICATION INFORMATION:
        (A) AUTHORS: Kang et al.
        (B) JOURNAL: Nature
        (C) VOLUME: 325
        (D) PAGES: 733
        (E) DATE: 1987

(iv) SEQUENCE DESCRIPTION: SEQ ID NO:1:

CTCTAGAACT AGTGGGTCGA CACGATGCTG CCCGGTTTG                              39

DIAGNOSTIC ASSAY FOR ALZHEIMER'S DISEASE BASED ON THE PROTEOLYSIS OF THE AMYLOID PRECURSOR PROTEIN

This application is a continuation of application Ser. No. 08/156,516, filed on Nov. 23, 1993, now abandoned, which is a continuation of application Ser. No. 07/865,167, filed Apr. 9, 1992, now abandoned.

BACKGROUND

The invention relates to methods of diagnosis for Alzheimer's Disease in humans. More particularly, the present invention is a diagnostic assay based on the detection of proteolysis of the precursor to the Alzheimer's Disease beta-amyloid protein in the presence of a sample of cerebrospinal fluid or blood obtained from a patient to be tested.

Alzheimer's Disease (hereinafter "AD") is a progressive, degenerative disorder of the brain, characterized by progressive atrophy, usually in the frontal, parietal and occipital cortices. The clinical manifestations of AD include progressive memory impairments, loss of language and visuospatial skills, and behavioral deficits (McKhan et al., 1986, Neurology 34:939–944). Overall cognitive impairment is attributed to degeneration of neuronal cells located throughout the cerebral hemispheres (Price, 1986, Annu. Rev. Neurosci. 9:489–5120).

Pathologically, the primary distinguishing features of the post-mortem brain of an AD patient are, 1) pathological lesions comprised of neuronal perikarya containing accumulations of neurofibrillary tangles; 2) cerebrovascular amyloid deposits; and 3) neuritic plaques. Both the cerebrovascular amyloid and the neuritic plaques contain a distinctive peptide simply designated, "A4" or "beta-amyloid".

Beta-amyloid is an insoluble, highly aggregating, small polypeptide of relative molecular mass 4,500, and is composed of 39 to 42 amino acids. Kang et al., 1987, Nature 325:733–736, described the beta-amyloid protein as originating from and as a part of a larger precursor protein. To identify this precursor, a full-length complementary DNA clone coding for the protein was isolated and sequenced, using oligonucleotide probes designed from the known beta-amyloid sequence. The predicted precursor contained 695 residues and is currently designated, "APP 695" (amyloid precursor protein 695).

APP 695 is the most abundant form of APP found in the human brain, but three other forms exist, APP 714, APP 751 and APP 770. The different length isoforms arise from alternative splicing from a single APP gene located on human chromosome 21 (Goldgaber et al., 1987, Science 235:877–880; Tanzi et al., 1987, Science 235:880–885).

Subsequent cloning of the gene encoding the APP proteins revealed that the A4 region was encoded on two adjacent exons, ruling out the possibility that A4 accumulation is the result of direct expression of an alternatively spliced mRNA. This implied that A4 accumulation must result from abnormal proteolytic degradation of the APP at sites both N- and C-terminal to the peptide region within the APP.

Recent studies have shown that APP fragments extending from the N-terminus of A4 to the C-terminus of the full length APP molecule (referred to hereinafter as the "C-100 fragment", because it is comprised of approximately 100 amino acids) are also capable of aggregation (Wolf et al., 1990, EMBO 9:2079–2084). Furthermore, overexpression of C-100 fragments in transgenic mice results in the accumulation of neurofibrillary tangles and neuritic plaque co-incident with neuronal degeneration (Kawabata et al., 1991, Nature 325:476–478). Collectively these data suggest that a single proteolytic cleavage of APP at the N-terminus of the A4 region is sufficient to initiate the pathophysiology associated with AD.

APP is also cleaved at a site within the A4 region in the physiological pathway for secretion of the APP extracellular domain (Esch et al., 1990, Science 2:1122–1124; Wang et al., 1991, J. Biol. Chem. 266:16960–16964). This pathway is operative in several cell lines and necessarily results in the destruction of the A4, amyloidic region of the precursor. Evidence that such a pathway is also operative in the human brain has been obtained (Palmert et al, 1989, Biochem. Biophys. Res. Comm. 165:182–188).

The enzymes responsible for the normal, non-pathological processing of APP have been termed "secretases". C-terminal fragments resulting from secretase action are smaller than the C-100 fragments (defined above) by 17 amino acids, and will hereinafter be referred to as the "physiological C-terminal fragment."

It has been postulated that the net pathological accumulation of A4 is controlled by the relative activity of the pathologic and physiologic pathways of APP degradation. It is uncertain whether the imbalance resulting in the dramatic increase in accumulation of A4 in the brains of AD patients results from a decrease in the activity of the secretases or an increase in the pathologic protease activity, or a combination of both.

Several studies have undertaken the purification and characterization of both the secretases and purported pathologic proteases. Initial studies utilized assays featuring synthetic peptide substrates that only mimicked the expected cleavage sites within APP. These assays failed to provide the necessary protease specificity, and the peptidase activities thus quantified were used without success to pursue the purification of candidate APP processing enzyme activities from human brain tissue. To date, no credible candidate protease (s) for either process have emerged, and the results of the various studies have been conflicting.

For example, the numerous available studies have proposed that the pathologic protease is: a lysosomal cathepsin, Cataldo et al., 1990, Proc. Natl. Acad. Sci USA 87:3861–3865; a calcium dependent serine protease, Abrahams et al., 1990, J. Neuropathol. Exp. Neurol., 49:333 (abstract); Calpain I, Siman et al., 1990, J. Neuroscience 10:2400–2411; a multicatalytic protease, Ishiura et al., 1989, FEBS. Lett. 257:388–392; or a chymotryptic-like serine protease, Nelson et al., 1990, J. Biol Chem. 265:3836–3843.

Similar inconsistencies have arisen in the efforts to identify the secretase, which has been claimed to be: a metallopeptidase, McDermott et al., 1991, Biochem. Biophys. Res. Comm. 179:1148–1154; an acetylcholinesterase associated protease, Small et al., 1991, Biochemistry 30:10795–10799; or Cathepsin B, Tagawa et al., Biochem. Biophys. Res. Comm. 177:377–387.

The general lack of success of past and current efforts to identify the nature of the APP processing enzymes have stemmed from poor specificity of the assays employed, and from the complex heterogeneity of proteases associated with the cerebral tissue.

The present invention arose from efforts aimed at identifying the APP processing enzymes using specific assays based on the proteolytic degradation of recombinant APP. It has been discovered that such assays have utility in the diagnosis of AD by the unexpected finding of substantially different levels of APP degrading enzyme activity in samples of cerebrospinal fluid (hereinafter "CSF") obtained from AD patients compared with healthy controls.

The present invention is an in vitro assay for detecting AD-related differences in the levels of proteolytic enzyme activity specific for APP 695 in a body fluid derived from a patient. It has been unexpectedly discovered that CSF derived from AD patients contain no detectable levels of protease activity or significantly and consistently lower levels of protease activity than corresponding control samples of CSF derived from non-AD individuals. Thus, this assay is suitable for use as a diagnostic for AD in humans, and would provide means of early detection as required for more effective early therapeutic intervention.

Based on available knowledge and data prior to the present disclosure, the logical expectation is for relatively increased protease activity resulting in C-100 fragments for fluids continuous with the CNS from AD patients. The results disclosed herein show the opposite, CSF from non-AD subjects show relatively and consistently higher enzyme activity resulting in the C-100 fragments.

Presently, the only means for conclusive confirmation of clinical diagnosis is post mortem examination of the brains of AD diagnosed patients for the presence of cerebrovascular amyloid deposits, neuritic plaques and neurofibrillary tangles. By contrast, the present assay can be performed on body fluid samples derived from live patients, to quantify protease activity.

Other reports of biochemical differences between control and AD patients which may be of potential diagnostic utility are known including, the detection of dermal amyloid deposits in AD using radioactive iodine substituted derivatives (U.S. Pat. No. 5,039,511); elevated plasma alpha-1-anti chymotrypsin levels in AD (Matsubara et al., 1990, Ann. Neurol. 28:561–567); and the presence of immunochemical markers such as A68, a 68 kDa protein expressed by degenerating neurons and detectable with the monoclonal antibody ALZ-50 (Wolozin et al., 1986, Science, 323:648–650).

U.S. Pat. No. 4,874,694, describes a method of testing CSF for non-specific peptides susceptable to protein kinase C-phosphorylation. Protein kinase C activity deviating from norm is said to be an indicator for a wide variety of neurological or psychiatric disorders, without any particular specificity.

Thus, there is a need in the art for a convenient diagnostic method which can confirm clinical indications of AD prior to the death of the patient. The large qualitative differences in activities obtained between control and AD patients in the present invention provides for a reliable clinical diagnostic method. The differences depend on enzymatic activity which offers the potential for further signal amplification by increasing the time period of incubation of the enzyme with the APP substrate.

Additionally, the format of the presently disclosed assays affords the capacity to process reasonably large numbers of samples and yields good sensitivity due to the immunochemical method of detection. Furthermore, the simplicity of the assay allows for ready adaptation for routine use by lab technicians and yields consistent, reproducible results. These and other improvements are described hereinbelow.

SUMMARY OF INVENTION

The present invention provides a method for use in the diagnosis of Alzheimer's Disease in which a sample of cerebrospinal fluid or blood taken from a patient (hereinafter referred to as the "test sample") is combined with an APP substrate and proteolytic cleavage of the APP substrate in the presence of said sample is detected. It has been found that test samples obtained from individuals known to be afflicted with Alzheimer's Disease lack a characteristic APP proteolytic activity exhibited by test samples obtained from control individuals.

The method can be performed under conditions in which essentially no detectable proteolytic cleavage is produced in the presence of test samples from AD individuals, whereby the absence of detectable proteolytic cleavage in the presence of the patient sample indicated affliction with Alzheimer's Disease.

Proteolytic cleavage of the APP substrate can be detected in a number of convenient manners, including the detection of polypeptide or peptide fragments produced by proteolysis of the substrate. Such fragments can be detected by any convenient means, such as by antibody binding. Another convenient method for detecting proteolytic cleavage is through the use of a chromogenic APP substrate whereby cleavage of the substrate reagent releases a chromogen, e.g., a colored or fluorescent, product.

Accordingly, the present invention further provides a test kit for use in the testing of a cerebrospinal fluid or blood sample of a patient as an aid in the diagnosis of Alzheimer's Disease, comprising one or more containers holding (a) an APP substrate, and (b) an antibody reagent, preferably comprising a detectable label such as an enzyme, which binds with a polypeptide or peptide fragment which is characteristic of proteolytic cleavage which occurs in the presence of samples from control individuals, but which is substantially not present in, or which is present at substantially lower levels in, test samples of individuals afflicted with Alzheimer's Disease.

Alternatively, the present invention provides a chromogenic substrate for use in the testing of a test sample from a patient as an aid in the diagnosis of Alzheimer's Disease. Such chromogenic substrate is formed of an APP substrate portion linked to a chromogenic indicator portion through a peptide linkage that is cleavable by protease present in cerebrospinal fluid or blood of control individuals but which is substantially not cleavable, or cleavable to a substantially lesser degree, in the presence of cerebrospinal fluid or blood of individuals afflicted with Alzheimer's Disease. Preferably, cleavage of such chromogenic APP substrate releases an colored indicator moiety.

DESCRIPTION OF THE INVENTION

Figure 1A:
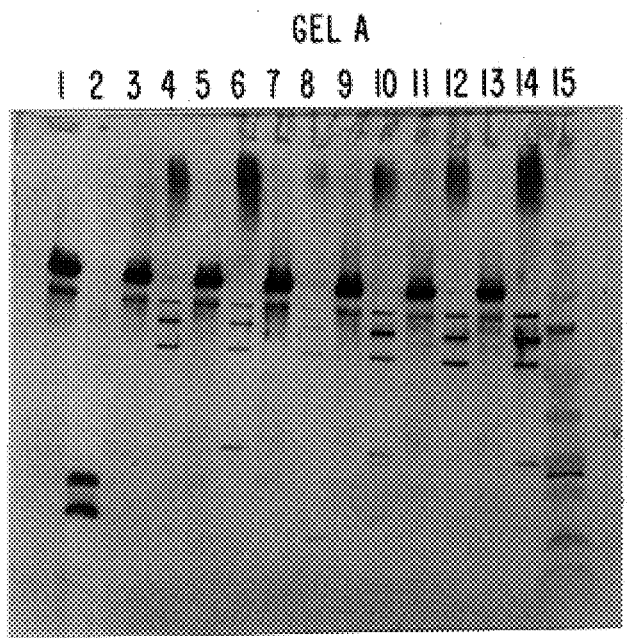
FIGS. 1A–1C show three gels which represent typical immunoblot analysis results for the present invention. The results depict the relative capacities of CSF, from control and Alzheimer's Disease patients, to catalyze the in vitro degradation of amyloid precursor protein to yield C-terminal APP fragments (denoted by the lower arrows in gels a, b, and c). The proteolytic activities of nine AD and five control patients are compared. The results show that while CSF from four of the five control cases contained detectable proteolytic activity only one of nine AD CSF samples possessed the same activity.

The present invention is based on the unexpected finding that cerebrospinal fluid of individuals afflicted with AD contain measurably lower levels of, or under particular conditions no detectable levels of, APP protease (or proteases with APP protease-like activity) relative to the level of APP proteolytic activity in cerebrospinal fluid of healthy or control individuals. For purposes hereof, control individuals are those who do not manifest clinical or pathological indications of AD. The phenomenon responsible for such decrease in APP proteolytic activity in AD test samples is not clear.

It is postulated that Alzheimer's Disease is due to a deficiency in the levels of the secretase enzyme which serves to cleave APP in such a fashion as to render it innacessible to the pathway of amyloidosis. In this regard it is possible that the enzymic activity measured in the present invention corresponds to the formation of the physiological C-terminal fragment by the secretase. This conclusion however is made less likely by the fact that the physiologic fragment would be approximately 17 amino acids smaller than C-100 and would not be expected to co-migrate with recombinant C-100, as has been observed in the present invention.

In any event, the unexpected observation provides the basis for a convenient and versatile method useful as an aid in the diagnosis of Alzheimer's Disease. Moreover, the finding is extendable to the testing of blood samples, particularly samples of peripheral blood, including plasma and serum, since various isoforms of APP are found in a variety of blood components, most notably platelets. Although obtainable by more invasive measures, cerebrospinal fluid may be the preferred test sample due to the presence of higher levels of APP proteolytic activity in normal CSF, as well as having to deal with protease inhibitors appearing in blood.

The APP substrate used in the present method comprises a site for the differential proteolytic cleavage observed between control individuals and AD patients. Accordingly, such APP substrate can be provided as a test reagent in a variety of forms. Although preferably derived from, or corresponding at least in part with the amino acid sequence of, APP 695, derivatives or analogs of other APP iosoforms (supra) are contemplated for use in the present method as well. APP 695 can be obtained by biochemical isolation or purification from natural sources such as described in Schubert et al., 1989, Proc. Natl. Acad. Sci. 86:2066; or by expression of recombinant DNA clones encoding the protein or a functional portion thereof (Knops et al., 1991, J. Bio. Chem. 266:7285; Bhasin et al., 1991, Proc. Natl. Acad. Sci. 88:10307).

As used herein, "APP substrate" shall mean full length APP, whether derived by isolation or purification from a biological source or by expression of a cloned gene encoding APP or its analogs, and fragments of any such protein, including fragments obtained by digestion of the protein or a portion thereof, fragments obtained by expression of a gene coding for a portion of the APP protein, and synthetic peptides having amino acid sequences corresponding to a portion of the APP protein. The aforesaid fragments of the APP protein will comprise a sequence of amino acids sufficient for recognition and cleavage by the pertinent proteolytic test sample activity (supra).

Isolation of APP from biological material usually will involve purification by conventional techniques such as chromatography, particularly affinity chromatography. Purified APP can be used to prepare monoclonal or polyclonal antibodies which can then be used in affinity purification according to conventional procedures. Resulting purified APP material can be further processed, e.g., fragmented, by chemical or enzymatic digestion. Useful fragments will be identified by screening for desired susceptibility to the pertinent proteolytic test sample activity (supra).

As previously stated, the APP substrate can also be prepared by expression of recombinant DNA clones coding for APP or a portion thereof. The cloned APP gene may itself be natural or synthetic, with the natural gene obtainable for cDNA or genomic libraries using degenerate probes based on known amino acid sequences (Kang et al., 1987, Nature 325:733). Other techniques for obtaining suitable recombinant DNA clones, as well as methods for expressing the cloned gene, will be evident to the worker in the field.

Furthermore, the APP substrate can be prepared to a convenient size by conventional peptide synthesis in correspondence with the deduced amino acid sequence of the desired APP isoform. In particular, based on amino acid analysis, overlapping peptides can be synthesized and tested for the pertinent proteolytic susceptibility. As useful peptides are found, smaller peptides can be prepared in order to map smaller reacting units, if desirable.

A variety of convenient methods are applicable to the detection of proteolytic cleavage of the APP substrate in the presence of the test sample. Several of the presently more preferred methods are described below, however, it will be recognized by the skilled worker in the field that many other methods can be applied to this step without departing from the inventive features hereof. In general, any method can be used for this purpose which is capable of detecting the occurrence of proteolytic cleavage of the APP substrate. Such can be afforded by appropriate design of the APP substrate such that cleavage produces a signal producing species, e.g., an optically responsive product such as a colored or fluorescent dye. Another principal approach involves the sensitive detection of one or more cleavage products such as by immunoassay. Such cleavage product or products to be detected is that which is characteristically produced by reaction of the APP substrate with test samples from control individuals compared to those with AD. Presently, such cleavage product is preferentially a C-terminal fragment of the APP substrate; however, any fragment which appears upon incubation with control samples but which is absent from, or appears in substantially lesser amounts in, as assay mixture comprising an AD test sample can be the object of detection.

The detection of one or more cleavage products characteristic of the differential proteolytic activity observed in control samples compared to AD samples, can be accomplished in many ways. One such method, which is further exemplified in the examples which follow, involves the procedure commonly known as Western blot. Typically, after the incubation of APP with test sample, gel electrophoresis is performed to separate the components resulting in the reaction mixture. The separated protein components are then transferred to a solid matrix such as a nitrocellulose membrane. An antibody specific to a fragment characteristic of control versus AD individuals is then reacted with the components fixed to the membrane and detected by addition of a secondary enzyme-labeled antibody conjugate. The location of the resulting bound conjugate is developed with a chromogenic substrate for the enzyme label.

A variety of immunoassay formats which are amenable to currently available diagnostic test systems can also be applied to the detection of APP fragments. Typically, the APP substrate will be incubated with the test sample and resulting intact APP rendered immobilized (such as by capture onto a solid phase), or alternatively, the test sample is incubated with an immobilized form of the APP substrate. Proteolytic cleavage characteristic of the control population compared to AD individuals is then detected by reacting the immobilized APP substrate with an antibody reagent directed to a portion of the APP substrate which is cleaved from the APP substrate or which defines the cleavage site. The antibody reagent can comprise whole antibody or an antibody fragment comprising an antigen combining site such as Fab or Fab', and can be of the monoclonal or polyclonal type. The detection of antibody reagent bound to the immobilized phase is indicative of the absence of the characteristic proteolytic cleavage and thus indicates affliction with AD. The detection of binding of the antibody reagent will generally involve use of a labeled form of such antibody reagent or use of a second, or anti-(antibody), antibody which is labeled.

Capture or immobilization of APP can be accomplished in many ways. An antibody can be generated specific to an epitope of APP which is not on the cleavable fragment. Such an antibody can be immobilized and used to capture or immobilize intact APP. Alternatively, a ligand or hapten can be covalently attached to APP and a corresponding immobilized receptor or antibody can be used to capture or immobilize APP. A typical ligand:receptor pair useful for this purpose is biotin:avidin. Examples of haptens useful for this purpose are fluorescein and digitoxigenin.

The solid phase on which the APP substrate is immobilized or captured can be composed of a variety of materials including microtiter plate wells, test tubes, strips, beads, particles, and the like. A particularly useful solid phase is magnetic or paramagnetic particles. Such particles can be derivatized to contain chemically active groups that can be coupled to a variety of compounds by simple chemical reactions. The particles can be cleared from suspension by bringing a magnet close to a vessel containing the particles. Thus, the particles can be washed repeatedly without cumbersome centrifugation or filtration, providing the basis for fully automating the assay procedure.

Labels for the primary or secondary antibody reagent can be selected from those well known in the art. Some such labels are fluorescent or chemiluminescent labels, radioisotopes, and, more preferably, enzymes for this purpose are alkaline phosphatase, peroxidase, and β-galactosidase. These enzymes are stable under a variety of conditions, have a high catalytic turnover rate, and can be detected using simple chromogenic substrates.

Proteolytic cleavage of the APP substrate can also be detected by chromatographic techniques which will separate and then detect the APP fragments. High pressure liquid chromatography (HPLC) is particularly useful in this regard. In applying this technique, a fluorescently tagged APP substrate is prepared. After incubation with the test sample, the reaction mixture is applied to the chromatographic column and the differential rate of migration of fluorescent fragments versus intact APP is observed.

EXAMPLE 1

Development of Chinese Hamster Ovary (CHO) call line expressing recombinant APP 695 a) Vector construction. A known 2.36 Kb NruI/SpeI fragment of APP 695 cDNA from FC-4 (Kang et al., supra) was filled in by the large fragment of *E. coli* DNA polymerase I and blunt-end inserted into the SmaI cloning site of KS Bluescript M13+(Stratagene Cloning Systems, La Jolla, Calif.) creating pMTI-5 (App 695 under the T3 promoter). A new optimal Kozak consensus DNA sequence was then created using site-specific mutagenesis (Kunkel et al., 1987, *Methods in Enzymology*, 154:367–382) with the oligo: 5'-CTCTAGAACTAGTGGGTCGACACGATGCTGCCC GGTTTG-3' (SEQ ID NO: 1) to create PMTI-39. This plasmid was next altered by site specific mutagenesis (Kunkel et al., Id.) to change the valine at position 614 to a glutamate (open reading frame numbering according to Kang et al., Id.).

The full length APP cDNA containing the optimal Kozak consensus sequence and Val to Glu mutation was then cut out of PMTI-39 with NotI and a HindIII partial digest. The 2.36 Kb APP 695 fragment was then gel purified and ligated into NotI/HindIII cut pcDNAINeo (Invitrogen Corp. San Diego, Calif.) to create PMTI 90 in which the APP 695 expression is placed under the control of the CMV promoter. The Val to Glu mutation was sequence confirmed and the vector used to stably transform CHO cells.

b) Generation of stable CHO call lines expressing APP 695 Rutenes. Chinese Hamster Ovary K-1 cells (ATCC CCL 61) were used for transfection with the APP 695 construct. Twenty micrograms of an expression plasmid containing APP 695 and a neomycin drug resistance marker were transfected into $1 \times 10^7$ CHO cells in 0.5 ml PBS by electroporation using a Bio-Rad Gene Apparatus (Bio-Rad Laboratories, Richmond, Calif.). A single pulse of 1200 V at 25 μf capacitance was administered to the cells.

Following electroporation, cells were incubated in ice for 10 minutes and collected by centrifugation. The cell pellet was resuspended in Alpha MEM, 10% fetal calf serum at a density of $5 \times 10^4$ cells/ml, and 1 ml aliquots were distributed into each well of five 24-well tissue culture cluster plates. After 48 hours incubation, cells containing the neomycin drug resistance marker were selected by addition of 1 ml of media containing 1 mg/ml Geneticin (GIBCO-BRL, Grand Island, N.Y.) and incubation was continued and bi-weekly changes of drug containing media.

Drug resistant cells were tested for APP 695 expression by Western blotting. Cells positive for APP 695 expression were cloned by limiting dilution, and individual clones were isolated and tested for APP 695 expression. A clone positive for APP 695 expression was subcultured and expanded into roller bottles for large scale production of APP 695 expressing cells and subsequent isolation of recombinant protein.

EXAMPLE 2

Development of expression vectors for the production of recombinant C-100 standard by transient infection of mammalian cells The C-100 peptide fragment contains the C-terminal portion of APP which spans from the N-terminus of the A4 peptide to the C-terminus of full length APP (see above, BACKGROUND section). The C-100 fragment is the purported initial degradation product leading to the ultimate formation of the A4 peptide.

Figure 1B:
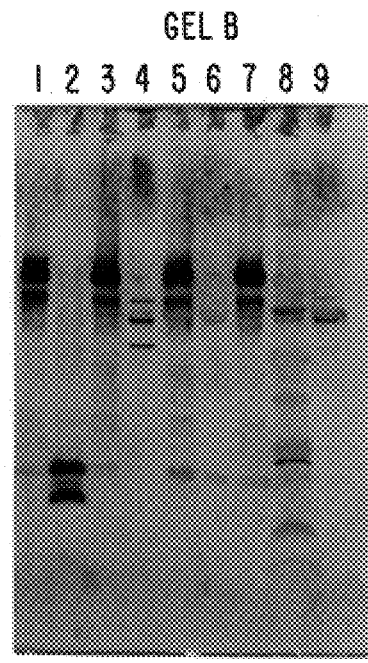
Figure 1C:
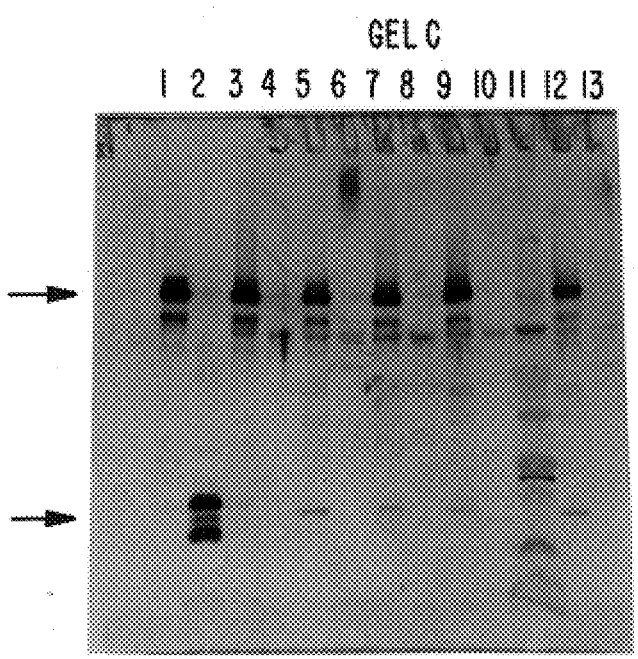

In one embodiment of the present invention, cell lysates from Hela S3 cells (ATCC CCL 2.2) expressing recombinant C-100 are analyzed in the immunoblot assay in parallel with the recombinant APP samples that have been incubated with CSF (see FIG. 1). The migration and detection of the C-100 fragments serves both as a size marker for the genesis of products formed by pathologic proteases as well as a positive control for the immunodetection of C-terminal APP fragments in general.

Comparison of the size of enzymically generated products with the size of the C-100 fragment can provide insights into whether or not the enzymically generated fragments result from cleavage close to the N-terminus of the A4 peptide or alternatively within the A4 segment as would be catalyzed by secretase.

a) Plasmid construction

Two methods were used to make plasmids for C-100 expression. Each plasmid shall be identified separately as either PMTI 73 or PMTI 100.

pKTX 73 Construction: The commercially available plasmid PUC-19 was digested with EcorI to eliminate its polylinkers. Commercially available PWE16 was then inserted into the digested PUC-19 to create PMTI 2300. PMTI 2301 was derived from PMTI 2300 following BamHI/Hind III digestion using an oligonucleotide adapter. The EcoRI promoter fragment of APP was inserted into the HindIII site of pMTI 2301 by blunt end ligation to produce PMTI 2307.

PMTI 2311 was generated by ligating the BamHI fragment from FC-4 (Kang et al., supra) into the BamHI site of PMTI 2307. The XhoI fragment from FC-4 was inserted into the XhoI site of PMTI 2311 to generate PMTI 2312. PMTI 2323 was generated by insertion of the 2.2 kb BglII/EcoRI fragment from the EcoRI genomic clone of the mouse metallothionein-I gene into the ClaI site of PMTI 2312. To generate minigene PMTI 2337, the sequences between the KpnI and BglII sites of PHTI 2323 were deleted and the clone was ligated using synthetic oligonucleotide adaptor, sp-spacer-A4.

PMTI 2337 was cut with Bam H1/SpeI and the fragment ligated into the Bam H1/XbaI restriction sites of bluescript KS (+) (Stratagene) to create PMTI 2371. PMTI 2371 was cut Hind III/NotI to release a 0.7 kb fragment coding for the terminal 100 amino acids of APP 695. Also encoded was the sequence for signal peptide. This insert was ligated into the Hind III/NotI site of pcDNAINEO (Invitrogen Corp.) to create the plasmid PMTI 73.

PKTI 100 Construction: PMTI 90 (see Example I) was cut XbaI/HindIII to release a 0.6 kb fragment again coding for the terminal 100 amino acids of APP 695 and this was ligated to the XbaI/HindIII site of pcDNAINEO to create PMTI 100. In each case vectors, inserts and plasmids were purified by methods known to those skilled in the art.

b) Transfection and expression of C-100 Fragment. Preparation for small scale expression of C-100 standard was initiated by seeding $5 \times 10^5$ cell Hela S1 cells in each well of a 6 well costar cluster (3.5cm diameter) 24 hours before use.

Sufficient vaccinia virus vTF7-3 was trypsin treated to infect at a multiplicity of 20 plaque forming units per cell, mixing an equal volume of crude virus stock and 0.25 mg/ml trypsin, then vortexed vigorously. The trypsin treated virus was incubated at 37° C. for 30 minutes, with vortexing at 10 minute intervals. Where clumps persisted, the incubation mixture was chilled to 0° C. and sonicated for 30 seconds in a sonicating water bath. The chilled sonication was repeated until no more clumps were detected.

The trypsin treated virus was then diluted with sufficient serum free DMEM for each well with Hela S1 cells to have 0.5 ml of virus. Medium was aspirated way, then the cells were infected with virus for 30 minutes, with rocking at 10 minutes intervals to distribute the virus.

Approximately 5 minutes before infection was ceased, fresh transfection mixture was prepared as follows: To each well was added 0.015 ml lipofection reagent (Betheseda Research Labs, Gathersburg, Md.) to 1 ml OPTIMEM (Betheseda Research Labs, Gathersburg, Md.) in a polystyrene tube, mixing gently. Vortex was avoided. Then, 3 μg CsCl purified DNA was added and mixed gently.

Virus mixture was aspirated from cells, then the transfection solution was introduced. The resulting mixture was incubated for three hours at 37° C. Each well was then overlaid with 1 ml of OPTIMUM and incubated at 37° C. in a $CO_2$ incubator overnight.

Cells were harvested at 20 hours post transfection by centrifugation, and lysates were prepared on ice with the addition of 0.2 ml of a lysis buffer which contained 1% Triton X-100, 10 μg/ml BPTI, 10 μg/ml Leupeptin, 200 mM Nacl, 10 mM HEPES, 1 mM $CaCl_2$, 1 mM $MgCl_2$, 1 mM EDTA, adjusted to pH 7.5. Complete lysis was monitored by light microscopy, and harvested immediately. Lysis took less than 1 minute to complete, with delay at this step causing lysis of nuclei resulting in a gelatinous mess.

Recombinant lysates were stored at −20° C. for later use. Preferably, recombinant lysates should be diluted 1:50, in (3X) SDS PAGE sample buffer which is devoid of 2-mercapto ethanol prior to freezing.

A comparison of the size of the proteins produced by expression with either PMIT 73 or PMTI 100 using SDS-PAGE/immunoblot with the APP C-terminal antibody was performed. The study showed that PMTI 100 directed the expression of a single immunoreactive band, whereas, PMTI directed the expression of three bands of similar molecular size. The band of intermediate size was less intense when compared to the upper and lower bands, and co-migrated with the single product band observed when using PMTI 100 to direct the expression.

The largest of the three bands produced by PMTI 73 was slightly larger than the single band observed with PMTI 100. Amino acid sequence analysis of the largest band from PMTI 73 expression showed that the signal peptide sequence was cleaved from the initial translation product to yield a C-100 fragment containing 5 extra amino acids at the N-terminus. Although our initial results in example 5 showed the result of a study in which the protein product of PMTI 73 was used as a migration marker, use of the protein encoded by PMTI 100 is preferred.

EXAMPLE 3

Preparation of Rabbit polyclonal antisera

Antisera were elicited to the C-terminal domain of human APP 695, and were prepared in accordance with the method as described in Buxbaum et al., 1990, Proc. Nat'l. Acad. Sci. 87:6003–6006. A synthetic peptide (hereinafter "B APP 645–694") corresponding to the COOH-terminal region of APP 695 was obtained from the Yale University, Protein and Nucleic Acid Chemistry Facility, New Haven, Conn.

β APP 645–694 was used to immunize rabbits to elicit polyclonal antibodies. Sera were screened by immunoblot analysis of lysates of *E. coli* that expressed a fusion protein including the amino acids 19 through 695 of human APP 695. Sera which were immunoreactive against the recombinant fusion protein were further screened for immunoprecipitating activity against [$^{35}$S] methionine-labeled APP 695, which was produced from β APP 695 cDNA by successive in vitro transcription (kit purchased from Stratagene, La Jolla, Calif.) and translation (reticulocyte lysate kit purchased from Promega Corp., Madison, Wis.).

EXAMPLE 4

Purification of APP 695 from recombinant CHO cells

All steps were performed at 0 to 4° C. unless indicated otherwise. Holo-APP 695 was detected by immunoblot analysis using an anti human APP 695 C-terminal antibody essentially as described in Example 5, below.

a) Isolation of plasma membranes. Whole cell pellets (179 g) from continuous culture of CHO cells in roller bottles were collected by centrifugation (1500 g×5 min), and resuspended to a total volume of 600 ml in 50 mM tris-HCl buffer pH 8.0 containing sodium chloride (30 mM), magnesium chloride (1 mM), EDTA (10 MM), PMSF (200 µg/ml), E-64 (42 µg/ml) and pepstatin (3.8 µg/ml). The cells were homogenized using a teflon potter (10 return strokes), then layered (25 ml per centrifuge tube) onto 10 ml of homogenization buffer containing 41% sucrose and devoid of the protease inhibitors EDTA, PMSF, E-64 and pepstatin. Following centrifugation (26,800 RPM×60 min, in a Beckman SW-28 rotor, the interfacial layer was carefully removed (approximately 150 ml in combined volume), diluted with an equal volume of homogenization buffer (minus protease inhibitors), resuspended with a teflon potter (3 return strokes), and recentrifuged as described above to yield a tightly packed pellet. The supernatant was decanted and the pellet resuspended in 100 ml total volume with 50 mM tris HCl pH 8.0 (teflon potter 3 return strokes). Recentrifugation (50,000 RPM×60 min in a Beckman 70 Ti rotor), yielded a pellet which was resuspended to a total volume of 57 ml in 50 mM tris HCl, pH 8.0.

b) Solubilization of Plasma Membranes. Thirty seven milliliters of the above resuspended CHO plasma membrane preparation were added sequentially to a cocktail of protease inhibitors and stock 20% (v/v) triton X-100 to achieve the following component concentrations: EDTA (1 mM), E-64 (24 µg/ml), PMSF (53 µg/ml), pepstatin A (11 µg/ml), and triton X-100 (2.2% v/v, final), in the homogenization buffer (total solubilization volume of 45 ml) described above. After gently rocking of the mixture at 4° C. for 30 min, the non-solubilized material was removed by centrifugation (50,000 RPM×40 min in a Beckman 70 Ti rotor). The supernatant containing solubilized holo-APP was filtered through a 0.45 µM disc filter.

c) Purification of solubilized holo-APP 69S by strong anion exchange chromatography. The above supernatant containing holo-APP 695 was diluted with an equal volume of distilled water and applied to a mono-Q RH 10/10 column previously equilibrated with 20 mM tris-HCl buffer pH 8.0 containing 0.1% triton X-100. Once loaded the column was eluted in a linear gradient of 0 to 1M NaCl contained within a total volume of 210 ml of equilibration buffer. The flow rate was maintained at 3 ml/min throughout. Proteins eluting between a conductivity range of 17 to 22 mmho (4° C.) contained the majority of immunoreactive APP 695, and were combined and dialyzed for 4 hours versus 2L of 5 mM tris-HCl pH 8.0 containing 0.025% triton X-100, and clarified to remove slight turbidity by centrifugation (26,800×60 min in a Beckman SW 28 rotor).

d) Keparin agarose chromatography. The clarified sample was applied to a column of heparin agarose (15×1.6 cm) previously equilibrated with dialysis buffer. Upon loading a light brown band formed within the top ⅓ of the column. Once loaded, 5 min fractions were collected (a flow rate of 1 ml/min was used throughout). The column was then eluted stepwise with 85 ml of equilibration in which the sodium chloride was successively adjusted to the following final concentrations: 0, 150, 300, 600, and 2000 mM. The majority of the immunodetectable holo-APP eluted at 600 mM NaCl, with the next quantitative fraction being recovered at 300 mM. The APP recovered at 300 mM and 600 mM NaCl were collected separately and stored in aliquots at −80° C. The APP used in the following studies were from the 300 mM fraction. The yield of partially pure APP from the 300 mM heparin agarose eluent was 5.5 µg (Bradford assay) per gram of wet CHO cell pellet.

EXAMPLE 5

The immunoblot assay for the detection of differences in the degradation of APP 695 catalyzed by control and AD COP a) Incubation of C8P vith APP i) CSF (5 µl) can be incubated with substrate APP 695 for between 24 to 48 hours. For this example, the 48 hour incubation period was chosen, and the other incubation parameters were: at 37° C. with 10.75 µl of recombinant human APP 695, which was adjusted to 140 mm final in MES buffer pH 6.5 by the addition of the required amount of 2M stock buffer. The final buffer concentration in the incubation being 95 mM, pH 6.5. The final concentration of partially pure APP preparation and MES buffer after mixing with CSF were 37 µg/ml and 95 mM, respectively, in a total reaction volume of 15.75 µl. During the incubation time, proteolytic degradation of some of the APP 695 occurs to yield lower molecular weight fragments.

ii) The proteolytic reaction was terminated by addition of 7.5 µl, of the following 3X Laemlie SDS-PAGE sample buffer: 1.5M Tris HCl, pH 8.45, containing 36% (v/v) glycerol and 12% (v/v) SDS, 10% (v/v) 2-mercaptoethanol, and trace bromophenal blue tracking dye. Samples were heated (100° C.×8 min), and then cooled.

b) SDB PAGE analysis

The reaction mixtures (15 µl) were applied to the wells of a 10 to 20% acrylamide gradient Tricine gel (routinely a 1.0 mm thick, 15 well Novex precast gel, Novex Experimental Technology, San Diego, Calif.). The gel was run under constant voltage conditions, and at 50 V until the sample enters the gel whereupon the voltage was raised to 100 V. Electrophosesis was discontinued when the tracking dye reaches to within 0.5 cm of the gel bottom. The gels were calibrated using prestained Mr markers ranging in Mr from 3 to 195 kDa (Bethesda Research Laboratories, Gaithersburg, Md.). Ten microliters each of a kit containing high and low molecular weight markers were mixed with 10 µl of 3X sample buffer, and treated as described in section (a)(ii).

c) Inmunoblotting i) The gel was then transferred to a mini trans-blot electrophoresis cell (Biorad Labs, Richmond, Calif.). Proteins were electro-blotted onto a ProBlott (TM) membrane (Applied Biosystems, Foster City, Calif.), for 1 hour at 100 V (constant), using the following transfer buffer maintained at 4° C.:20 mM Tris HCl buffer pH 8.5 containing 150 mM glycine and 20% (v/v) methanol.

ii) The ProBlott membrane was removed and placed in 15 ml of blocking buffer of the following composition for 1 hour at room temperature: 5% (w/v) non-fat dried milk in 10 mM Tris HCl buffer pH 8.0 containing 150 mM NaCl.

d) Immunodetection of APP and C-terminal degradation products

The membrane was transferred to 15 ml of blocking buffer containing a 1:1000 dilution of rabbit polyclonal antiserum elicited to a synthetic human APP 695 C-terminal peptide immunogen and incubated at 4° C. over night.

The membrane was rinsed with three successive 15 ml volumes of blocking buffer with gentle shaking for 5 minutes. The membrane was then transferred to 15 ml of blocking buffer containing a 1:1000 dilution of alkaline phosphatase-coupled Goat anti-Rabbit IgG (Fisher Scientific, Pittsburgh, Pa.), and incubated at room temperature for 90 minutes. The membrane was then rinsed with three successive 15 ml volumes of blocking buffer with gentle shaking for 10 minutes.

The membrane was next washed with three consecutive 15 ml volumes of alkaline phosphatase buffer for 5 minutes each, comprising: 100 mM Tris HCl pH 9.5, containing 100 mM NaCl and 5 MM $MgCl_2$. The gel was next incubated in the dark with 15 ml of 100 mm Tris HCl pH 9.5, containing 100 mM NaCl, 5 mM $MgCl_2$ and 50 μl of BCIP substrate (50 mg/ml, Promega, Madison, Wis.) and 99 μl of NBT substrate (50 mg/ml, Promega). Incubation was continued until there was no apparent further intensification of low Mr immunoreactive bands (typically 3 hours at room temperature).

The gel was then rinsed with deionized water and dried. A typical end result of such analysis is shown in FIG. 1, which is further tabulated in Tables 1, 2 and 3, and explained hereinbelow.

RESULTS of a typical analysis comparing activity in control and AD CSF

To examine potential differences between the levels of APP degrading proteases in the CSF of control and AD patients, the following experiment was performed:

CSF from a total of nine (9) persons diagnosed with AD at post mortem (average age at death was 77 years, range 69 to 84 years, average autolysis time is 4.38 hours, n=9), and five (5) persons diagnosed as not having AD based on clinical assessment and post mortem examination (average age was 72 years, range 57 to 85 years, n=4, average autolysis time is 3.5 hours, n=5) were individually tested for APP degrading activity using the assay conditions described in Example 5, above.

The following controls were performed:
i) APP was incubated in the presence of reaction buffer and the absence of CSF to assess the extent of APP degradation arising from trace proteases within the APP preparation itself (FIG. 1), lane 1 for each of gels a, b and c, see also Tables 1–3, below);
ii) cell lysate containing authentic recombinant C-100 fragment derived by Example 2 was applied to each gel (FIG. 1, lane 2 in each of gels a, b and c, in an amount equivalent to that present in one microliter of original Hela S3 cell culture;
iii) for each incubation containing CSF and APP, a corresponding incubation in which the APP was omitted was performed to determine if the CSF contained endogenous immunoreactive bands which would complicate the interpretation of products derived from recombinant APP proteolysis. This APP control was analyzed in an adjacent electrophoretic lane to the incubation containing the complete system.

TABLE 1

(legend for "gel a" in FIG. 1)

| CASE CODE | APP 695 (+/−) | SAMPLE DIAG-NOSIS | SEX | AGE (YRS) | AUTOLYSIS TIME (HRS) |
|---|---|---|---|---|---|
| 1 | — | APP only | — | — | — |
| 2 | — | C-100 | — | — | — |
| 3 89-35 | + APP | AD | M | 78 | 9 |
| 4 89-35 | − APP | | | | |
| 5 89-34 | + APP | AD | M | 80 | 4 |
| 6 89-34 | − APP | | | | |
| 7 89-29 | + APP | AD | M | 80 | 4 |
| 8 89-29 | − APP | | | | |
| 9 89-26 | + APP | AD | M | 76 | 3 |
| 10 89-26 | − APP | | | | |
| 11 89-25 | + APP | AD | F | 78 | 5.5 |
| 12 89-25 | − APP | | | | |
| 13 89-08 | + APP | AD | M | 75 | 3.5 |
| 14 89-08 | − APP | | | | |

TABLE 1-continued (legend for "gel a" in FIG. 1)

| CASE CODE | APP 695 (+/−) | SAMPLE DIAG-NOSIS | SEX | AGE (YRS) | AUTOLYSIS TIME (HRS) |
|---|---|---|---|---|---|
| 15 Mr Markers* | | | | | |

*Mr Markers are: Myosin H-chain (196 kDa), phosphorylase B (106 kDa), bovine serum albumin (71 kDa), Ovalbumin (44 kDa), Carbonic anhydrase (28 kDa), betalacroglobulin (18 kDa), lysozyme (15 kDa) bovine trypsin inhibitor (5.8 kDa) and Insulin A and B chains (3 kDa).
Note: The upper arrows in FIG. 1 show the position of uncoverted APP 695 and the lower arrows show the position of migration of the enzymically generated band. Notice the absence of the lower Mr band in the AD cases, but its presence in 4 of 5 controls.

TABLE 2

(legend for "gel b" in FIG. 1)

| CASE CODE | APP 695 (+/−) | SAMPLE DIAG-NOSIS | SEX | AGE (YRS) | AUTOLYSIS TIME (HRS) |
|---|---|---|---|---|---|
| 1 | — | APP only | | | |
| 2 | — | C-100 | | | |
| 3 90-05 | + APP | AD | F | 77 | 2.5 |
| 4 90-05 | − APP | | | | |
| 5 90-01 | + APP | AD | F | 84 | 2.5 |
| 6 90-01 | − APP | | | | |
| 7 89-41 | + APP | AD | M | 69 | 5.5 |
| 8 Mr Markers* | | | | | |
| 9 89-41 | − APP | | | | |

TABLE 3

(legend for "gel c" in FIG. 1)

| CASE CODE | APP 695 (+/−) | SAMPLE DIAG-NOSIS | SEX | AGE (YRS) | AUTOLYSIS TIME (HRS) |
|---|---|---|---|---|---|
| 1 | — | APP only | | | |
| 2 | — | C-100 | | | |
| 3 89-43 | + APP | Control | F | 85 | 2 |
| 4 89-43 | − APP | | | | |
| 5 89-37 | + APP | Control | M | X | 6 |
| 6 89-37 | − APP | | | | |
| 7 89-24 | + APP | Control | M | 71 | 2.5 |
| 8 89-24 | − APP | | | | |
| 9 89-22 | + APP | Control | F | 73 | 4 |
| 10 89-22 | − APP | | | | |
| 11 Mr Markers* | | | | | |
| 12 89-11 | + APP | Control | F | 57 | 3 |
| 13 89-11 | − APP | | | | |

X = The precise age at death could not be determined.
* = Mr Markers are the same as for Table 1, above.

The results of the experimental comparison are shown in FIG. 1. The legends in Tables 1, 2 and 3 provide, in addition to the contents of each immunoblot lane, a detailed description of the patient diagnosis, sex, age at death, and time after death which elapsed before sampling of CSF (autolysis time). All samples were frozen either on dry ice or at −80° C. as soon as possible after removal and stored as such until analyzed.

The arrows on FIG. 1 designate the regions of interest in the assessment of degradation of APP to low molecular size C-terminal fragments. The upper arrow denotes the migration of the undegraded recombinant APP, which co-migrates with the phosphorylase B marker suggesting an apparent size of around 110 kDa. The lower arrow marks the position of migration of C-100.

This fragment migrated slightly ahead of lysozyme, suggesting an apparent molecular mass of around 14 kDa. In four out of five cases using CSF from different control cases, incubation of the CSF with APP caused the formation of an immunoreactive band which co-migrated within the size range corresponding to recombinant C-100 (FIG. 1, gel c, lanes 5, 7, 9 and 12).

By sharp contrast, this band was found to be completely absent in eight of nine incubations using AD CSF (FIG. 1, gel a, lanes 3, 5, 7, 9 and 11; and gel b, lanes 3, 5 and 7) and only faintly visible in the incubation of CSF from the ninth AD patient (gel a, lane 13). The band is not present in any of the control incubations containing APP without CSF (lane 1, gels a, b and c) showing that it is not derived from proteolytic activities found within the APP preparation itself. Furthermore, none of the CSF samples when incubated without recombinant APP showed the presence of the fragment (gel a, lanes 4, 6, 8, 10, 12 and 14; gel b, lanes 4, 6 and 9; gel c, lanes 4, 6, 8, 10 and 13), showing that the fragment had to be derived from the breakdown of the recombinant APP.

Thus, the data shows a significant difference between control and AD CSF in the levels of this C-terminal APP product formed specifically by incubation of CSF with the APP substrate.

(a) providing an APP substrate comprising a substrate selected from the group consisting of APP 695, APP 714, APP 751, and APP 770;

(b) combining said APP substrate with a sample of body fluid obtained from said patient, said body fluid sample being selected from the group consisting of cerebrospinal fluid and blood contained from said patient;

(c) detecting the amount of said cleavage product produced as a result of the proteolytic cleavage of said APP substrate in the presence of said sample;

(d) comparing the amount of said cleavage product produced in (c) to that which is produced as a result of the proteolytic cleavage of said APP substrate in the presence of cerebrospinal fluid or blood samples from control individuals; and (e) using the comparison in (d) in the diagnosis of probable affliction with Alzheimer's Disease, wherein the probable affliction of said patient with Alzheimer's Disease is indicated by either (i) a total lack of the production of said cleavage product by said patient or (ii) a reduction in the amount of said cleavage product that is produced by said patient as compared to that produced by said control individuals.

2. The method of claim 1 wherein said body fluid sample is cerebrospinal fluid.

---

---

What is claimed is:

1. A method for use in the diagnosis of probable affliction with Alzheimer's Disease in a patient, by which method the proteolytic cleavage of a cleavage product from an amyloid precursor protein (APP) substrate is assayed, said cleavage product being approximately 10–14 kDa and co-migrating with recombinant C-100 by sodium dodecyl sulphate page analysis, said method comprising the steps of:

3. The method of claim 1 wherein said amyloid precursor protein (APP) substrate comprises a recombinantly expressed polypeptide.

4. The method of claim 1 wherein said amyloid precursor protein (APP) substrate comprises a synthetic peptide.

5. The method of claim 1 wherein said cleavage product is detected by antibody binding.

* * * * *